United States Patent
Esmaili et al.

(10) Patent No.: US 9,945,801 B1
(45) Date of Patent: Apr. 17, 2018

(54) MONITORING THE ACTIVITY OF REFORMING CATALYST

(71) Applicant: Air Products and Chemicals, Inc., Allentown, PA (US)

(72) Inventors: Ali Esmaili, Emmaus, PA (US); Joshua David Isom, Allentown, PA (US); Suyash Singh, Annandale, NJ (US)

(73) Assignee: Air Products and Chemicals, Inc., Allentown, PA (US)

( * ) Notice: Subject to any disclaimer, the term of this patent is extended or adjusted under 35 U.S.C. 154(b) by 69 days.

(21) Appl. No.: 15/293,653

(22) Filed: Oct. 14, 2016

(51) Int. Cl.
*G01K 1/00* (2006.01)
*G01N 25/28* (2006.01)
*C01B 3/38* (2006.01)

(52) U.S. Cl.
CPC .............. *G01N 25/28* (2013.01); *C01B 3/38* (2013.01); *C01B 2203/0233* (2013.01); *C01B 2203/16* (2013.01)

(58) Field of Classification Search
CPC ...... F01N 11/002; F01N 5/02; F02D 19/0623; F02D 19/0671
USPC ......................................... 702/127, 130–134
See application file for complete search history.

(56) References Cited

U.S. PATENT DOCUMENTS

| 5,006,425 A | 4/1991 | Takabayashi |
| 8,984,864 B2 * | 3/2015 | Cockle ............... B01D 53/9445 60/276 |
| 2012/0291424 A1 | 11/2012 | Inuzuka et al. |
| 2016/0297727 A1 * | 10/2016 | Modarresi ................ C01B 3/38 |

FOREIGN PATENT DOCUMENTS

| EP | 1 835 141 A2 | 9/2007 |
| EP | 2 246 294 A1 | 11/2010 |
| WO | 02 070873 A1 | 9/2002 |

OTHER PUBLICATIONS

Hawkins, G., "Steam Reforming Practical Operation", http://s3.amazonaws.com/academia.edu.documents PDF not attached due to copyright restrictions.

Hawkins, Gerard B., "Steam Reforming (ATM) Approach to Equilibrium", published Sep. 25, 2013; http://www.slideshare.net/GerardBHawkins/steam-reforming-atm-approach-to-equilibrium PDF not attached due to copyright restrictions.

* cited by examiner

*Primary Examiner* — An Do
(74) *Attorney, Agent, or Firm* — Bryan C. Hoke, Jr.

(57) ABSTRACT

A method and system for determining changes in the catalytic activity of reforming catalyst where an outlet temperature of the catalytic reactor is measured and a temperature approach to equilibrium calculated based on the measured outlet temperature. The temperature approach to equilibrium is compared to an empirical model-based temperature approach to equilibrium calculated for the same operating conditions, the comparison showing changes in the catalytic activity of the reforming catalyst.

19 Claims, 4 Drawing Sheets

MONITORING THE ACTIVITY OF REFORMING CATALYST

BACKGROUND

The present invention relates generally to catalytic steam-hydrocarbon reforming and more specifically to determining changes in the catalytic activity of the reforming catalyst used in catalytic steam-hydrocarbon reformers. The determination of changes may be for decreases in the catalytic activity of the reforming catalyst as well as for increases due to refurbishment events or catalyst replacement.

Steam-hydrocarbon reforming catalysts are subject to numerous types of degradation, including sintering, carbon formation, and sulfur poisoning. Catalyst degradation results in a decline in the catalytic activity, which in turn reduces the efficiency and economic performance of the hydrogen or synthesis gas production facility. It is therefore important to be able to monitor the activity of the reforming catalyst and quantify the extent of reduced catalytic activity so that catalyst regeneration activities can be scheduled and failure of the reformer can be avoided.

Steam-hydrocarbon reforming catalysts may be refurbished in various ways, including replacement, partial replacement, and steaming. It is important to be able to receive an empirical confirmation that catalyst refurbishment activities have resulted in a significant improvement in catalytic activity, thereby allowing for continued operation of the reforming plant before refurbishment activities are repeated again.

In the prior art, a temperature approach to equilibrium has been used as an indicator for reduced activity of reforming catalyst. This approach requires collection of a sample of the reformate from the reformer furnace and offline measurement of the composition of the sample. The outlet temperature is estimated from the equilibrium constant for the water-gas shift reaction and the composition of the reformate at the outlet. The equilibrium temperature is calculated from the equilibrium constant for the steam reforming reaction at the measured composition for the reformate at the outlet. The temperature difference is the temperature approach to equilibrium.

For a fixed reformer operating condition, a small temperature approach to equilibrium (close to zero) means that the catalyst activity is high and that little degradation of the catalyst has occurred. On the other hand, a large temperature approach to equilibrium means that the catalyst activity has decreased and that the catalyst degradation has occurred. Although the temperature approach to equilibrium is widely used as a diagnostic tool for steam-hydrocarbon reformers, it has a major deficiency. In addition to being sensitive to catalyst degradation, the temperature approach to equilibrium also exhibits significant sensitivities to normal variations in furnace operating conditions, such as production rate, steam-to-carbon molar ratio, reformer operating temperature, and reformer operating pressure.

These variables all affect the conventionally calculated temperature approach to equilibrium, even for constant reforming catalyst conditions. The sensitivity of the conventionally calculated temperature approach to equilibrium to process conditions severely limits its utility as a diagnostic tool for catalyst degradation.

Industry desires new and/or improved methods for monitoring the catalytic activity of reforming catalyst for both increased catalytic activity and decreased catalytic activity.

Industry desires methods for monitoring the catalytic activity of reforming catalyst that is sensitive to changes in the catalyst activity but relatively insensitive to normal changes in process operating conditions.

Industry desires methods for monitoring catalytic activity of reforming catalyst using existing process data, and preferably process data which does not require a sample to be collected and analyzed offline.

Industry desires methods for enabling determination of changes in activity of reforming catalyst, in particular, for enabling determination of reduced activity of reforming catalyst, that is sensitive to changes in the catalyst activity but relatively insensitive to normal changes in process operating conditions.

BRIEF SUMMARY

The present invention relates to a method and system for determining changes in the catalytic activity of reforming catalyst, either or both of increased catalytic activity and/or decreased catalytic activity.

There are several aspects of the invention as outlined below. In the following, specific aspects of the invention are outlined below. The reference numbers and expressions set in parentheses are referring to an example embodiment explained further below with reference to the figures. The reference numbers and expressions are, however, only illustrative and do not limit the aspect to any specific component or feature of the example embodiment. The aspects can be formulated as claims in which the reference numbers and expressions set in parentheses are omitted or replaced by others as appropriate.

Aspect 1. A method comprising:
(a) introducing a reformer feed gas mixture (15) comprising at least one hydrocarbon and steam into one or more catalytic reactors (20) comprising the reforming catalyst in a reformer (10), each of the one or more catalytic reactors (20) having an inlet and an outlet, reacting the reformer feed gas mixture (15) in a steam-methane reforming reaction and water-gas shift reaction under reaction conditions effective to form a reformate (25) comprising $H_2$, CO, $CH_4$, and $H_2O$, and withdrawing the reformate (25) from the one or more catalytic reactors (20);

wherein for a plurality of times, the method comprises (b) measuring an outlet temperature, $T_{outlet}$, representative of a temperature at the outlet of the one or more catalytic reactors (20) for each time of the plurality of times;

(c) determining a temperature approach to equilibrium for the steam-methane reforming reaction at the outlet of the one or more catalytic reactors (20) for each time of the plurality of times using the measured outlet temperature, $T_{outlet}$;

(d) calculating an empirical model-based temperature approach to equilibrium from reformer operating data (acquired at each time of the plurality of times) and an empirical model based on historical operating data for a model reformer for each time of the plurality of times, wherein the model reformer is the reformer (10) or another reformer (of the same type); and (e) comparing the temperature approach to equilibrium to the calculated empirical model-based temperature approach to equilibrium for each time of the plurality of times;

wherein steps (b) through (e) are repeated for the plurality of times.

Aspect 2. The method according to aspect 1 wherein steps (b) through (e) are performed at least once per month, or at least once per week, or at least once per day, or at least once per hour, or at least once per minute during operation of the reformer (10).

Aspect 3. The method according to aspect 1 or aspect 2 wherein, for each time of the plurality of times, the step of determining the temperature approach to equilibrium for the steam-methane reforming reaction comprises:

determining a reformate composition representative of the reformate withdrawn from the one or more catalytic reactors (20);

calculating an equilibrium temperature, $T_{equilibrium}$, from an equilibrium constant for the steam-methane reforming reaction at the reformate composition representative of the reformate withdrawn from the one or more catalytic reactors (20); and wherein the temperature approach to equilibrium is calculated from the outlet temperature, $T_{outlet}$, and the equilibrium temperature, $T_{equilibrium}$.

Aspect 4. The method of aspect 3 wherein the temperature approach to equilibrium, $\Delta T_{approach}$, is expressed by the equation $\Delta T_{approach} = T_{outlet} - T_{equilibrium}$.

Aspect 5. The method according to aspect 3 or aspect 4 wherein the reformer feed gas mixture is formed from a hydrocarbon feed and the steam, and wherein the step of determining the reformate composition representative of the reformate withdrawn from the one or more catalytic reactors (20) comprises:

determining a hydrocarbon feed composition representative of a composition of the hydrocarbon feed via a composition measurement;

determining a flow rate of the hydrocarbon feed a via flow rate measurement of the hydrocarbon feed;

determining a flow rate of the steam via a flow rate measurement of the steam; and calculating the reformate composition using chemical element flow rate balances, the representative hydrocarbon feed composition, the flow rate of the hydrocarbon feed, the flow rate of the steam, and a water-gas shift equilibrium constant evaluated at the measured outlet temperature, $T_{outlet}$.

Aspect 6. The method according to any one of aspects 3 to 5 further comprising:

measuring a reformate pressure representative of a pressure at the outlet of the one or more catalytic reactors (20), wherein the equilibrium temperature is calculated using the measured reformate pressure.

Aspect 7. The method according to any one of aspects 3 to 6 wherein the reformer feed gas mixture is formed from a $H_2$ feed in addition to being formed from the hydrocarbon feed and the steam, and wherein the step of determining the reformate composition representative of the reformate withdrawn from the one or more catalytic reactors (20) comprises:

determining a flow rate of the $H_2$ feed; and wherein the reformate composition is calculated also using the flow rate of the $H_2$ feed.

Aspect 8. The method according to any one of aspects 3 to 7 further comprising:

measuring a methane concentration representative of a concentration of methane in the reformate withdrawn from the one or more catalytic reactors (20);

wherein the reformate composition is calculated also using the representative methane concentration.

Aspect 9. The method according to any one of aspects 3 to 8 further comprising:

measuring a flow rate representative of a flow rate of the reformate, for example a dry-basis flow rate for the reformate;

wherein the reformate composition is calculated also using the representative flow rate of the reformate.

Aspect 10. The method according to any one of aspects 1 to 9 wherein the empirical model is formulated from historical outlet temperatures, $T_{outlet, historical}$, for the model reformer for a historical plurality of times, and calculated historical equilibrium temperatures, $T_{equilibrium, historical}$, for the model reformer for the historical plurality of times.

Aspect 11. The method according to aspect 10 wherein the historical equilibrium temperatures, $T_{equilibrium, historical}$, are calculated from the equilibrium constant for the steam-methane reforming reaction at historical reformate compositions representative of reformate withdrawn the one or more catalytic reactors of the model reformer for the historical plurality of times.

Aspect 12. The method according to aspect 10 or aspect 11 wherein the empirical model is formulated from additional historical operating data including an historical reformate pressure representative of the pressure at the outlet of the one or more catalytic reactors, $P_{outlet, historical}$, an historical flow rate of the steam, $n_{steam, historical}$, and an historical flow rate of the feedstock, $n_{feedstock, historical}$, each for the historical plurality of times.

Aspect 13. The method according to any one of aspects 10 to 12 wherein coefficients for the empirical model are determined by regressing $\Delta T_{empirical, historical}$ as a function of the historical outlet temperatures, $T_{outlet, historical}$, the historical reformate pressures representative of the pressure at the outlet of the one or more catalytic reactors, $P_{outlet, historical}$, the historical flow rate of the steam, $n_{steam, historical}$, preferably using a steam-to-carbon molar ratio, and the historical flow rate of the feedstock, $n_{feedstock, historical}$.

Aspect 14. The method according to aspect 13 wherein the function is a linear or non-linear equation with the coefficients determined by regression of the historical operating data, where $\Delta T_{empirical, historical} = T_{outlet, historical} - T_{equilibrium, historical}$ for the regression.

Aspect 15. The method according to aspect 14 wherein an empirical model-based temperature approach to equilibrium, $\Delta T_{empirical}$, is calculated with the coefficients determined by regression for the measured outlet temperature, $T_{outlet}$, a measured reformate pressure, $P_{outlet}$, representative of the pressure and the outlet of the one or more catalytic reactors, a flow rate of the steam, $n_{steam}$, preferably using a steam-to-carbon molar ratio, and a flow rate of the feed stock, $n_{feedstock}$, for each time of the plurality of times.

Aspect 16. The method according to any one of aspects 1 to 15 wherein the one or more catalytic reactors (20) are catalyst-containing reformer tubes in a reformer (10) wherein the reformer (10) comprises a plurality of catalyst-containing reformer tubes.

Aspect 17. The method according to aspect 16 wherein the reformer (10) is a reformer furnace, the method further comprising:

combusting a fuel (5) with an oxidant gas (7) in a combustion section (30) of the reformer furnace (10) external to the plurality of catalyst-containing reformer tubes (20) under conditions effective to combust the fuel (5) to form a combustion product gas (35) and generate heat to supply energy for reacting the reformer feed gas mixture (15) inside the plurality of catalyst-containing reformer tubes (20), and withdrawing the combustion product gas (35) from the combustion section (30).

Aspect 18. The method according to any one of aspects 1 to 17 wherein step (e) comprises:
  calculating a characteristic operational value ($\Delta T_{redisual}$) from the temperature approach to equilibrium and the calculated empirical model-based temperature approach to equilibrium, the characteristic operational value including the difference and/or the ratio of the temperature approach to equilibrium and the calculated empirical model-based temperature approach to equilibrium; and
  determining whether a change in the characteristic operational value represents an objective increase or decrease in the catalytic activity of the reforming catalyst.

Aspect 19. A method for determining decreased and/or increased activity of reforming catalyst comprising:
  the method of any one of aspects 1 to 18 wherein steps (b) through (e) are repeated during a time period where the temperature approach to equilibrium relative to the empirical model-based temperature approach to equilibrium for each time of the plurality of times differs by an amount for a selected period of time, the amount and selected period of time determined to indicate decreased and/or increased activity of the reforming catalyst.

Aspect 20. The method according to aspect 19 wherein steps (b) through (e) are repeated two or more times during the selected period of time.

Aspect 21. The method according to aspect 19 or aspect 20 wherein the amount determined to indicate decreased activity of the reforming catalyst is an amount corresponding to an increase in a value of a residual temperature to equilibrium, $\Delta T_{residual}$, of 3° C. or more during the selected period of time, where $\Delta T_{residual} = \Delta T_{approach} - \Delta T_{empirical}$, where $\Delta T_{approach} = T_{outlet} - T_{equilibrium}$, and corresponds to the temperature approach to equilibrium determined in step (c), where $T_{outlet}$ is the measured temperature representative of the temperature at the outlet of the one or more catalytic reactors (20), where $T_{equilibrium}$ is a temperature calculated from an equilibrium constant for the steam-methane reforming reaction at a reformate composition representative of the reformate withdrawn from the one or more catalytic reactors (20), and where $\Delta T_{empirical}$ corresponds to the calculated empirical model-based temperature approach to equilibrium.

Aspect 22. The method according to any one of aspects 19 to 21 wherein the amount determined to indicate increased activity of the reforming catalyst is an amount corresponding to a decrease in a value of a residual temperature to equilibrium, $\Delta T_{residual}$, of 3° C. or more during the selected period of time, where $\Delta T_{residual} = \Delta T_{approach}\ \Delta T_{empirical}$, where $\Delta T_{approach} = T_{outlet} - T_{equilibrium}$, and corresponds to the temperature approach to equilibrium determined in step (c), where $T_{outlet}$ is the measured temperature representative of the temperature at the outlet of the one or more catalytic reactors (20), where $T_{equilibrium}$ is a temperature calculated from an equilibrium constant for the steam-methane reforming reaction at a reformate composition representative of the reformate withdrawn from the one or more catalytic reactors (20), and where $\Delta T_{empirical}$ corresponds to the calculated empirical model-based temperature approach to equilibrium.

Aspect 23. A system for determining changes in the catalytic activity of reforming catalyst in one or more catalytic reactors (20) in a reformer (10), the one or more catalytic reactors (20) each having an inlet and an outlet, where a reformer feed gas mixture (15) is reacted in a steam-methane reforming reaction and water-gas shift reaction to form a reformate (25) comprising $H_2$, CO, $CH_4$, and $H_2O$, the system comprising:
  a temperature sensor (26) operable to measure an outlet temperature, $T_{outlet}$, representative of a temperature at the outlet of the one or more catalytic reactors (20), the temperature sensor (26) configured to transmit temperature information relating to the measured outlet temperature;
  a computing device (200) operable to receive operating information from the reformer furnace (10) including the temperature information from the temperature sensor (26), the computing device (200) operable to determine a temperature approach to equilibrium for the steam-methane reforming reaction at the outlet of the one or more catalytic reactors (20) over a period of time and for a plurality of times, the computing device (200) operable to calculate an empirical model-based temperature approach to equilibrium from an empirical model based on historical operating data for the reformer (10) or another reformer of the same type for each time of the plurality of times, the computing device (200) capable of providing an output suitable for comparing the temperature approach to equilibrium to the calculated empirical model-based temperature approach to equilibrium for each time over the period of time in order to monitor the activity of the reforming catalyst.

Aspect 24. The system according to aspect 23 wherein the computing device (200) is operable to perform the method according to any one of aspects 1 to 22.

Aspect 25. The system according to aspect 23 or aspect 24, the system further comprising:
  one or more sensors operable to obtain at least a subset of the operating information from the reformer and configured to transmit at least the subset of the operating information to the computing device (200).

Aspect 26. The system according to aspect 25 wherein the one or more sensors include a pressure sensor (27) operatively disposed to determine an outlet pressure representative of the pressure at the outlet of the one or more catalytic reactors (20), the pressure sensor (27) operatively connected to the computing device (200), wherein the operating information received by the computing device (200) includes the outlet pressure representative of the pressure at the outlet of the one or more catalytic reactors (20).

Aspect 27. The system according to any one of aspects 23 to 26 the system further comprising a chemical analyzer (76) operatively disposed to measure a composition of a sample representative of a hydrocarbon feed (75) where the reformer feed gas mixture (15) comprises the hydrocarbon feed (75), the chemical analyzer (76) operatively connected to the computing device (200) wherein the operating information received by the computing device (200) includes the composition of the sample.

Aspect 28. The system according to aspect 27, the system further comprising a flow meter (77) operatively disposed to measure a flow rate of the hydrocarbon feed (75), the flow meter (77) operatively connected to the computing device (200), wherein the operating information received by the computing device (200) includes the flow rate of the hydrocarbon feed (75).

Aspect 29. The system according to any one of aspects 23 to 28, the system further comprising a flow meter (152) operatively disposed to measure a flow rate of steam (151) where the reformer feed gas mixture (15) comprises the steam (151), the flow meter (152) operatively connected to the computing device (200), wherein the operating information received by the computing device (200) includes the flow rate of the steam (151).

Aspect 30. The system according to any one of aspects 23 to 29, the system further comprising a (reformate) chemical analyzer (96) operatively disposed to measure a concentration representative of at least one component in the reformate (25), the chemical analyzer (96) operatively connected to the computing device (200), wherein the operating information received by the computing device (200) includes the concentration representative of the at least one component in the reformate (25).

Aspect 31. The system according to aspect 30 wherein the at least one component includes methane.

Aspect 32. The system according to any one of aspects 23 to 31, the system further comprising a flow meter (98) operatively disposed to measure a flow rate representative of a flow rate of the reformate (95), for example a reformate dry-basis flow rate, the flow meter (98) for measuring the representative flow rate of the reformate operatively connected to the computing device (200), wherein the operating information received by the computing device (200) includes the representative flow rate of the reformate (95).

Aspect 33. The system according to any one of aspects 23 to 32, the system further comprising a flow meter (108) operatively disposed to measure a flow rate of a hydrogen feed (106) where the reformer feed gas mixture (15) comprises the hydrogen feed (106), the flow meter (108) operatively connected to the computing device, wherein the operating information received by the computing device (200) includes the flow rate of the hydrogen feed (106).

Aspect 34. The system according to any one of the aspects 23 to 33 wherein the computing device (200) is a programmable logic controller.

Aspect 35. The system according to any one of aspects 23 to 34 wherein the one or more catalytic reactors are catalyst-containing reformer tubes, wherein the reformer (10) comprises a plurality of the catalyst-containing reformer tubes (20).

DETAILED DESCRIPTION OF THE PREFERRED EMBODIMENTS

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention, it being understood that various changes may be made in the function and arrangement of elements without departing from scope of the invention as defined by the claims.

The articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The adjective "any" means one, some, or all indiscriminately of whatever quantity.

The term "and/or" placed between a first entity and a second entity includes any of the meanings of (1) only the first entity, (2) only the second entity, and (3) the first entity and the second entity. The term "and/or" placed between the last two entities of a list of 3 or more entities means at least one of the entities in the list including any specific combination of entities in this list. For example, "A, B and/or C" has the same meaning as "A and/or B and/or C" and comprises the following combinations of A, B and C: (1) only A, (2) only B, (3) only C, (4) A and B and not C, (5) A and C and not B, (6) B and C and not A, and (7) A and B and C.

The phrase "at least one of" preceding a list of features or entities means one or more of the features or entities in the list of entities, but not necessarily including at least one of each and every entity specifically listed within the list of entities and not excluding any combinations of entities in the list of entities. For example, "at least one of A, B, or C" (or equivalently "at least one of A, B, and C" or equivalently "at least one of A, B, and/or C") has the same meaning as "A and/or B and/or C" and comprises the following combinations of A, B and C: (1) only A, (2) only B, (3) only C, (4) A and B and not C, (5) A and C and not B, (6) B and C and not A, and (7) A and B and C.

The term "plurality" means "two or more than two."

For the purposes of simplicity and clarity, detailed descriptions of well-known devices, circuits, and methods are omitted so as not to obscure the description of the present invention with unnecessary detail.

The present invention relates to a method and system for determining changes in the catalytic activity of reforming catalyst in a catalytic reactor, such as a catalytic steam reforming furnace. The catalytic reactor may be used for generating hydrogen and/or synthesis gas. The method and system will be described with reference to FIG. 1 showing an exemplary process flow diagram of a production facility for generating hydrogen and/or synthesis gas.

Figure 1:
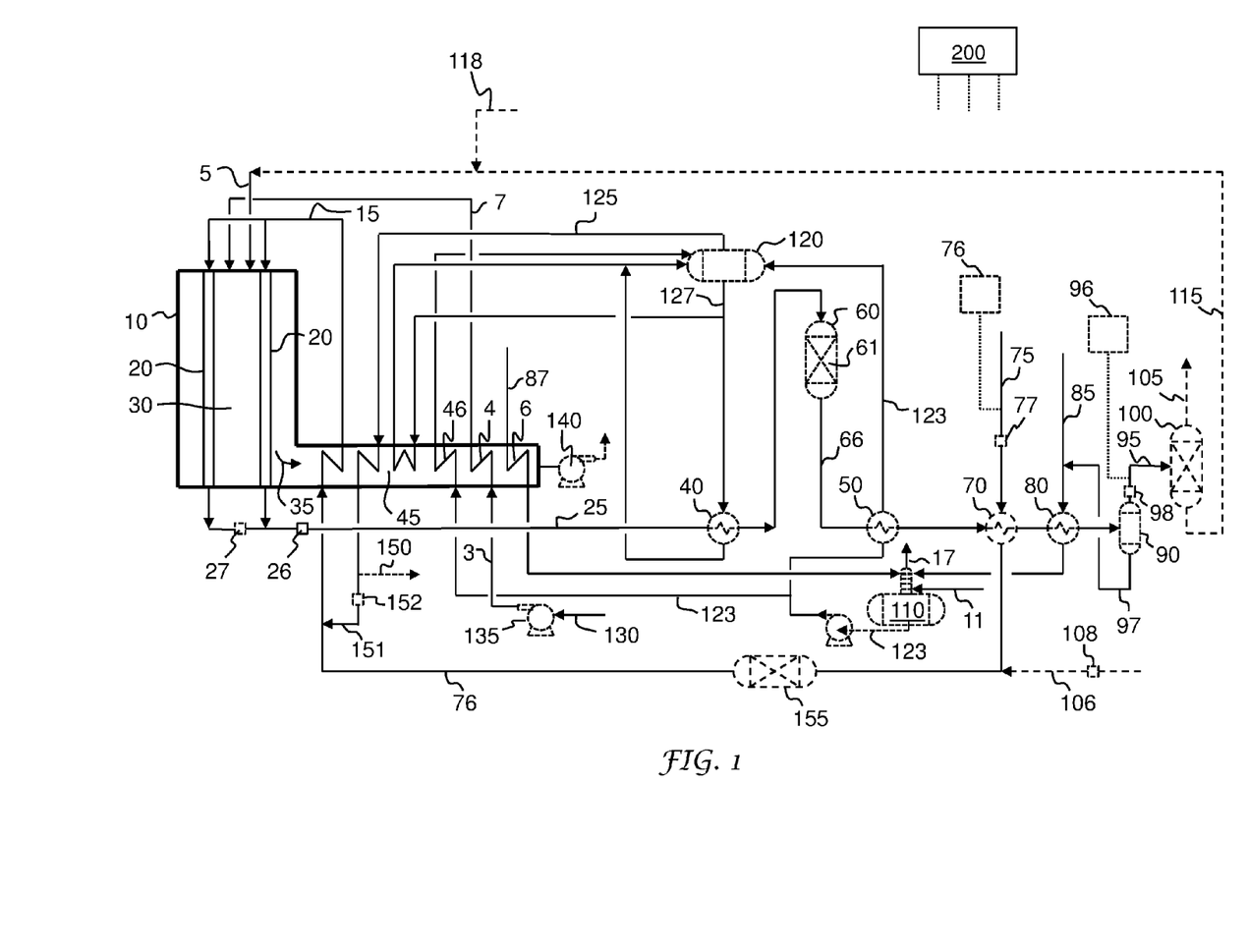
FIG. 1 is a process flow diagram of a hydrogen production process.

While the method and system are described with reference to a catalytic steam reforming furnace such as shown in FIG. 1, the method and system are applicable to other types of reformers, for example, reformers with radiant and convective reforming as disclosed in U.S. Pat. No. 6,793,700B2, and tube-in-tube reformers as disclosed in U.S. Pat. Nos. 5,639,431, 5,938,800, 4,909,808, and catalyzed heat exchanger reformer as disclosed in U.S. Pat. No. 6,117,578.

Catalytic steam reforming, also called steam methane reforming (SMR) or steam reforming, is defined as any process used to convert reformer feedstock to synthesis gas by reaction with steam over a catalyst. Synthesis gas, commonly called syngas, is any mixture comprising hydrogen and carbon monoxide. The reforming reaction is an endothermic reaction and may be described generally as $C_nH_m + n\ H_2O \rightarrow n\ CO + (m/2+n)\ H_2$. The water-gas shift reaction $CO + H_2O \rightarrow CO_2 + H_2$, an exothermic reaction, also takes place in the reactor.

A production facility for generating hydrogen and/or synthesis gas is a reformer and associated equipment for the production of hydrogen and/or synthesis gas. Associated equipment may include adiabatic prereformers, heat exchangers, pumps, fans, water-gas shift reactors, pressure swing adsorbers, condensers, boilers, steam drums, desulphurizers, deaerators, headers, manifolds, piping, etc.

In the present method, a reformer feed gas mixture 15 is introduced into one or more catalytic reactors 20 in reformer 10, each of the one or more catalytic reactors 20 having an inlet and an outlet. The reformer feed gas mixture 15 comprises at least one hydrocarbon and steam and is reacted in a steam-methane reforming reaction and water-gas shift reaction under reaction conditions effective to form a reformate 25 comprising $H_2$, CO, $CH_4$, and $H_2O$. The reformate 25 is withdrawn from the one or more catalytic reactors 20.

The reformer 10 may be a reformer furnace 10. Catalytic steam reforming takes place in reformer furnace 10. A reformer furnace, also called a catalytic steam reformer, or a steam methane reformer, is defined herein as any fired furnace used to convert feedstock containing elemental hydrogen and carbon to synthesis gas by a reaction with steam over a catalyst with heat provided by combustion of a fuel. The one or more catalytic reactors 20 may be catalyst-containing reformer tubes. Reformer furnaces with a plurality of catalyst-containing reformer tubes, i.e. tubular reformers, are well known in the art. Suitable materials and methods of construction are known. Catalyst in the catalyst-containing reformer tubes may be any suitable catalyst known in the art, for example, a supported catalyst comprising nickel.

The reformer feed gas mixture 15 comprises a hydrocarbon feedstock 75 and steam 151. Hydrocarbon feedstock may be natural gas, methane, naphtha, propane, refinery fuel gas, refinery off-gas, or other suitable reformer feedstock known in the art. Suitable operating temperatures range from 350° C. to 650° C. at the inlet and 750° C. to 950° C. at the outlet. Suitable pressures range from 1 to 50 atm. Preferred operating conditions for a catalytic steam reformer are known in the art. The hydrocarbon feedstock 75 may be heated and introduced along with hydrogen 106 into a hydrodesulphurization unit 155 to remove sulfur from the hydrocarbon feedstock for forming the reformer feed gas mixture 15. Hydrogen 106 for hydrodesulphurization may be added to the feedstock before or after heating the hydrocarbon feedstock 75. Hydrogen product 105 made by the hydrogen production facility may be used to provide hydrogen 106.

As used herein, a reformate is any mixture comprising hydrogen and carbon monoxide formed from the reforming reaction of a hydrocarbon and steam.

In a reformer furnace 10, a fuel 5 is combusted with an oxidant gas 7 in a combustion section 30 of the reformer furnace 10 external to the plurality of catalyst-containing catalytic reactors 20 (reformer tubes) under conditions effective to combust the fuel 5 to form a combustion product gas 35 comprising $CO_2$ and $H_2O$ and generate heat to supply energy for reacting the reformer feed gas mixture 15 inside the plurality of catalyst-containing reformer tubes 20. The combustion product gas 35 is then withdrawn from the combustion section 30 of the reformer furnace 10.

Any suitable burner may be used to introduce the fuel 5 and the oxidant gas 7 into the combustion section 30. Combustion of the fuel 5 with the oxidant gas 7 generates heat to supply energy for reacting the reformer feed gas mixture 15 inside the plurality of catalyst-containing reformer tubes 20. The combustion product gas 35 is withdrawn from the combustion section 30 of the reformer furnace 10 and passed to the convection section 45 of the reformer furnace 10 to supply heat to other process streams.

The combustion section 30 (also called the radiant, radiation, or radiative section) of the reformer furnace is that part of the reformer furnace containing the plurality of catalyst-containing reformer tubes 20. The convection section 45 of the reformer furnace 10 is that part of the reformer furnace 10 containing heat exchangers other than the plurality of catalyst-containing reformer tubes 20. The heat exchangers in the convection section may be for heating process fluids other than reformate 25 from the plurality of catalyst-containing reformer tubes 20, such as water/steam, air 130, pressure swing adsorption unit by-product gas 115, reformer feed gas mixture 15 prior to introduction into the catalyst-containing reformer tubes 20, prereformed reformer feed gas (not shown), etc. The convection section 45 may also, if desired, contain a convective prereformer (not shown).

Furnace conditions effective to combust the fuel 5 may comprise a furnace temperature ranging from 600° C. to 1500° C. and a pressure ranging from 98 kPa to 101.4 kPa (absolute). Actual flame temperatures are generally higher. The temperature may be as measured by a thermocouple, an optical pyrometer, or any other calibrated temperature measurement device known in the art for measuring furnace temperatures. The pressure may be as measured by any suitable pressure sensor known in the art, for example a pressure gauge as available from Mensor.

The fuel 5 may be formed from a by-product gas 115 from a pressure swing adsorption unit 100 and a supplemental fuel 118. By-product gas 115 from a pressure swing adsorption unit 100 is often called pressure swing adsorber tail gas, and supplemental fuel 118 is often called trim fuel. The by-product gas 115 and/or the supplemental fuel 118 may be heated by indirect heat transfer with the combustion product gas 35 and/or the reformate 25 before being used as fuel. The by-product gas 115 and/or the supplemental fuel 118 may be heated to a temperature ranging from 100° C. to 260° C. By-product gas 115 and supplemental fuel 118 may be blended and introduced together through a burner to the combustion section 30, or they may be introduced separately through different ports in the burner. Alternatively, the by-product gas 115 may be introduced through the primary burner and the supplemental fuel 118 may be introduced through lances near the burner.

The oxidant gas 7 is a gas containing oxygen and may be air, oxygen-enriched air, oxygen-depleted air such as gas turbine exhaust, industrial grade oxygen, or any other oxygen-containing gas known for use in a reformer furnace 10 for combustion. For example, as shown in the FIG. 1, air 130 may be compressed in forced draft fan 135, heated by the combustion product gas 35 in heat exchanger 4, and passed to the reformer furnace 10 as oxidant gas 7. Alternatively, (not shown) the air may be heated by a hot water/steam stream where the hot water/steam stream is heated by the combustion product gas 35.

Combustion product gas 35 may heat a number of different process streams in the convection section 45 of the reformer furnace 10. The combustion product gas 35 may heat the streams in various different configurations (order of heating). FIG. 1 shows an exemplary heat exchange network, although any suitable heat exchange network can be used with the present invention.

In FIG. 1, the combustion product gas 35 heats the reformer feed gas mixture 15 and then superheats steam stream 125 from steam drum 120. A portion 151 of the superheated steam may be used to form the reformer feed gas mixture 15 and another portion used to form a steam product 150 (i.e. export steam). After heating the steam, the combustion product gas then heats a portion of boiler feed water stream 127 from steam drum 120 in a heat exchanger to form a two-phase mixture of steam and water of which at least a portion is returned to the steam drum 120. The combustion product gas 35 then heats a water stream 123 from deaerator 110 after which the combustion product gas 35 heats compressed air stream 3 from compressor 135. Make up water stream 87 is heated by the combustion product gas 35 in heat exchanger 6 and passed to deaerator 110. After heating the make up water stream 87, the combustion product gas 35 is passed to an induced draft fan 140 and exhausted.

Reformate 25 withdrawn from the one or more catalytic reactors 20 may be passed to shift reactor 60 containing shift catalyst 61. The reformate 25 may exchange heat with any number of streams before being passed to the shift reactor 60. For example, the reformate 25 withdrawn from the one or more catalytic reactors 20 may be passed to heat exchanger 40 (a so-called waste heat boiler) where the reformate 25 heats a portion of boiler feed water stream 127 thereby forming a two-phase water and steam stream that is reintroduced into steam drum 120.

In the shift reactor 60, the reformate 25 is reacted in the presence of a shift catalyst 61 under reaction conditions sufficient to shift the reformate 25 to form additional $H_2$ in the reformate 25. Additional hydrogen gas may be obtained by the catalytic reaction of carbon monoxide and steam. This reaction is exothermic and is commonly referred to as the water-gas shift reaction or shift reaction: $CO + H_2O \rightarrow CO_2 + H_2$. The reaction is affected by passing carbon monoxide and water through a bed of a suitable catalyst. The reaction conditions effective to form additional hydrogen in the reformate 25 may comprise a second temperature ranging from 190° C. to 500° C. and a second pressure ranging from 203 kPa to 5,066 kPa (absolute).

Any suitable shift catalyst may be used. The shift reactor may be a so-called high temperature shift (HTS), low temperature shift (LTS), medium temperature shift (MTS), or combination. One or more shift reactors may be used.

For high temperature shift, an inlet temperature in the range 310° C. to 370° C., and an outlet temperature in the range 400° C. to 500° C. are typical. Usually an iron oxide/chromia catalyst is used for high temperature shift. High temperature shift may be preferred for the present process.

For low temperature shift, an inlet temperature in the range 190° C. to 230° C., and an outlet temperature in the range 220° C. to 250° C. are typical. Usually a catalyst comprising metallic copper, zinc oxide, and one or more other difficulty reducible oxides such as alumina or chromia is used for low temperature shift For medium temperature shift, an inlet temperature in the range 190° C. to 230° C. and an outlet temperature of up to 350° C. are typical. A suitably formulated supported copper catalyst can be used for medium temperature shift.

A combination may include a sequence of high temperature shift, cooling by indirect heat exchange, and low temperature shift. If desired, either shift stage can be subdivided with interbed cooling.

In the exemplary embodiment shown in FIG. 1, after passing through the shift reactor 60, the reformate 25 is passed to heat exchanger 50 where the reformate 25 heats a stream of boiler feed water 123 that is withdrawn from deaerator 110. The reformate 25 is then passed to heat exchanger 70 where hydrocarbon feedstock 75 is heated and reformate 25 is cooled. Reformate is then passed to heat exchanger 80 to heat a second water feed stream 85 by indirect heat transfer the reformate 25, thereby cooling the reformate 25.

The second water feed stream 85, typically called makeup water, may be distilled water, treated water (decalcified, filtered, etc.) or other suitable water known in the art. The heated water stream 85 is passed to deaerator 110 and forms the boiler feed water 123. Low pressure steam 11 is introduced into deaerator 110 to assist with stripping dissolved gases from the condensate and make-up water. A vent stream 17 is withdrawn from the deaerator and comprises steam and gases formed from the dissolved gases.

To reduce VOC emissions from the hydrogen production facility, the deaerator vent streams from deaerator 110 may be injected into the reformer furnace 10 as described in the "Report on Emission Limits for Rule 1189—Emissions from Hydrogen Plant Process Vents," South Coast Air Quality Management District, Jun. 7, 2001 (http//www3.aqmd.gov/hb/attachments/2002/020620b.doc), and "Final Environmental Assessment: Proposed Rule 1189—Emissions from Hydrogen Plant Process Vents" SCAQMD No. 1189JDN021199, South Coast Air Quality Management District Dec. 17, 1999 (http://www.aqmd.gov/docs/default-source/ceqa/documents/aqmd-projects/2000/final-ea-for-proposed-amended-rule-1189.doc?sfvrsn=4).

The reformate 25 may be passed to a trim cooler (not shown) to condense at least a portion of the water in the reformate to form condensed water and a water-depleted reformate gas.

The condensed water is separated from the water-depleted reformate gas in separator 90 to form water condensate 97 from at least a portion of the condensed water. Water condensate 97 is blended with the second water feed stream 85. A slip stream of condensed water may be removed from the separator, if desired.

The water-depleted reformate is passed to a pressure swing adsorption unit 100 where the water-depleted reformate is separated to form a hydrogen-containing product gas 105 and a pressure swing adsorption unit by-product gas 115, also called PSA tail gas, and PSA purge gas. The fuel combusted in the combustion section 30 of the reformer furnace 10 may be formed from at least a portion of the pressure swing adsorption unit by-product gas 115.

The pressure swing adsorption unit 100 may be operated using any known pressure swing adsorption cycle. Pressure swing adsorption cycles are well-known in the art and the various steps are described for example in U.S. Pat. No. 9,381,460, incorporated herein by reference. Specific pressure swing adsorption cycles are provided in companion articles "Pressure Swing Adsorption cycles for 4 to 7 adsorption beds," IP.com number 000241449, Apr. 29, 2015, and "Pressure Swing Adsorption cycles for 7 or more adsorption beds," IP.com number 000241619, May 18, 2015.

The method is characterized by repeatedly carrying out a number of steps over a period of time and for a plurality of times to monitor the activity of the reforming catalyst in the one or more catalytic reactors 20.

The method may be applied to monitor the activity of reforming catalyst in a single catalytic reactor (e.g. reformer tube), a group of catalytic reactors (e.g. group of reformer tubes), or all of the catalytic reactors (e.g. reformer tubes) in the reformer.

A first of the characterizing steps includes measuring an outlet temperature, $T_{outlet}$, representative of a temperature at the outlet of the one or more catalytic reactors 20 for each time of the plurality of times. The outlet temperature representative of the temperature at the outlet of one or more catalytic reactors 20 may be measured at the outlet of one catalytic reactor, or in a subheader receiving reformate from more than one catalytic reactor feeding the subheader, or in the main header receiving reformate from all of the catalytic reactors in a reformer. In the case where the temperature is measured at the outlet of only a single catalytic reactor, the method would monitor the catalytic activity of the reforming catalyst in that single catalytic reactor. In the case where the temperature is measured in the subheader receiving reformate from a subset of catalytic reactors, the method would monitor the collective catalytic activity of the reforming catalyst in that subset of catalytic reactors. In the case where the temperature is measured in the main header receiving reformate from all of the catalytic reactors in the reformer furnace, the method would monitor the collective catalytic activity of the reforming catalyst for all of the catalytic reactors in the reformer furnace.

It is well recognized that the measured outlet temperature is not a precise measure of the real outlet temperature for catalytic reactors due to the accuracy limitations of the temperature sensor and heat losses in the system. And while the measured outlet temperature is not a reliable measure for determining the species concentrations from equilibrium constant calculations, it is useful in the present method, since any bias is applied throughout.

A second of the characterizing steps includes determining a temperature approach to equilibrium for the steam-methane reforming reaction at the outlet of the one or more catalytic reactors 20 for each time of the plurality of times using the measured outlet temperature, $T_{outlet}$. The temperature approach to equilibrium relates the measured outlet temperature to the equilibrium temperature, $T_{equilibrium}$, corresponding to the composition of the reformate, and may conveniently be defined, $\Delta T_{approach} = T_{outlet} - T_{equilibrium}$, although other expressions are possible to describe the temperature approach to equilibrium. The equilibrium temperature, $T_{equilibrium}$, for the reforming reaction may be calculated from any suitable equation for the equilibrium constant for the reforming reaction and a determined reformate composition representative of the reformate withdrawn from the one or more catalytic reactors 20 (i.e. the partial pressures, or mole fractions of $H_2$, $CO$, $CH_4$, and $H_2O$).

From the definition of the equilibrium constant for the steam methane reforming reaction, it can be determined:

$$K_{SR}(T_{equilibrium}) = \frac{\left(\frac{\dot{n}_{H_2}}{\dot{n}_{total}}\right)^3 \left(\frac{\dot{n}_{CO}}{\dot{n}_{total}}\right)}{\left(\frac{\dot{n}_{CH_4}}{\dot{n}_{total}}\right)\left(\frac{\dot{n}_{H_2O}}{\dot{n}_{total}}\right)} \left(\frac{P_{outlet}}{P^o}\right)^2, \quad (Eq.\ 1)$$

where $\dot{n}$ is the molar flow rate of the specified species of the reformate, $P_{outlet}$ is the outlet pressure, $P^o$ is the standard state pressure, for example 100 kPa (1 bar), and $\dot{n}_{total}$ is the total molar flow rate of the reformate, $$\dot{n}_{total} = \dot{n}_{CH4} + \dot{n}_{CO2} + \dot{n}_{CO} + \dot{n}_{N2} + \dot{n}_{H2} + \dot{n}_{H2O} \quad (Eq.\ 2)$$

at the outlet of the one or more catalytic reactors 20.

The equilibrium temperature can be calculated from any known equation for the equilibrium constant for the steam methane reaction, for example, $$\ln(K_{SR}) = C_1 \times \ln(T) + \frac{C_2}{T} + C_3 + C_4 \times T + C_5 T^2 + C_6 T^3 \quad (Eq.\ 3)$$

where $C_1$=8.611124, $C_2$=-2.264801E4, $C_3$ (P in bar abs)=-2.898252E1, $C_4$=-4.980062E-3, $C_5$=3.977411E-7, and $C_6$=2.013436E-11, as provided by Rostrup-Nielsen, Concepts in Syngas Manufacture, Imperial College Press, Catalytic Science Series, Vol. 10, p 317, 2011.

The reformate composition representative of the reformate withdrawn from the one or more catalytic reactors 20 may be measured in a chemical analyzer, for example as described in U.S. Pat. Appl. No. 2016/0131631, or determined from other reformer furnace measurements as described below.

The reformate composition representative of the reformate withdrawn from the one or more catalytic reactors 20 may be determined through a calculation using chemical element flow rate balances and a number of common furnace measurements, for example a hydrocarbon feedstock composition measurement, a flow rate measurement of the hydrocarbon feedstock, a flow rate measurement of the steam, and the measured outlet temperature.

Referring to FIG. 1, the composition of the hydrocarbon feedstock 75 may be measured using a chemical analyzer 76, such as a gas chromatograph, and the flow rate of hydrocarbon feedstock 75 may be measured using a flow meter 77. The flow rate of steam 151 forming the reformer feed gas mixture 15 may be measured using flow meter 152. The flow rate of hydrogen 106 to the hydrodesulphurization unit 155, if present, may be measured using flow meter 108.

The reformate composition representative of the reformate withdrawn from the one or more catalytic reactors 20 may be calculated using a carbon mass/mole balance for the reformer:

$$\dot{n}_{feedstock}(y_{CH_4} + 2y_{C_2H_6} + 3y_{C_3H_8} + 4y_{C_4H_{10}} + y_{CO_2}) = \dot{n}_{CO_2} + \dot{n}_{CH_4} + \dot{n}_{CO}; \quad (Eq.\ 4)$$

an oxygen mass/mole balance for the reformer:

$$2\dot{n}_{feedstock}y_{CO_2} + \dot{n}_{steam} = 2\dot{n}_{CO_2} + \dot{n}_{CO} + \dot{n}_{H_2O}; \quad (Eq.\ 5)$$

a hydrogen mass/mole balance for the reformer:

$$2\dot{n}_{H_2,feed} + \dot{n}_{feedstock}(4y_{CH_4} + 6y_{C_2H_6} + 8y_{C_3H_8} + 10y_{C_4H_{10}}) + 2\dot{n}_{steam} = 2\dot{n}_{H_2O} + 4\dot{n}_{CH_4} + 2\dot{n}_{H_2}; \text{ and} \quad (Eq.\ 6)$$

an nitrogen mass/mole balance for the reformer:

$$2\dot{n}_{feedstock}y_{N_2} = 2\dot{n}_{N_2}. \quad (Eq.\ 7)$$

where $\dot{n}_{H_2,feed}$ is the molar flow rate of the hydrogen feed 106 to the hydrodesulphurization unit 155, if present, $\dot{n}_{feedstock}$ is the molar flow rate of the hydrocarbon feedstock 75, $\dot{n}_{steam}$ is the molar flow rate of steam 151, $\dot{n}_{CO_2}$ is the molar flow rate of $CO_2$ in the reformate 25, $\dot{n}_{CH4}$ is the molar flow rate of $CH_4$ in the reformate, $\dot{n}_{CO}$ is the molar flow rate of CO in the reformate, $\dot{n}_{H2O}$ is the molar flow rate of $H_2O$ in the reformate, and $y_i$, is the mole fraction of the respective component, i, in the hydrocarbon feedstock.

Equations 4-7 are for an exemplary hydrocarbon feedstock 75 that includes methane through butane. The equations can be easily modified for fewer or additional species in the hydrocarbon feedstock.

The methane slip is another parameter often measured. The reformate composition at the outlet of the one or more catalytic reactors may be calculated using a measurement representative of the methane concentration, such as determined from the methane slip. The dry gas methane concentration after the separator (knock-out drum) 90 and prior to introducing the reformate into the pressure swing adsorption unit 100 may be measured using chemical analyzer 96, which may comprise a metal oxide semiconductor sensor, such as Model M2A 65-2649RK-CH4 available from RKI Instruments. The shift reactor doesn't react the methane in the reformate and the molar flow rate of methane doesn't change from the outlet of the reformer to the inlet of the pressure swing adsorption unit 100. Then, $$\dot{n}_{CH_4} = \dot{n}_{CH_4, dry} = y_{CH_4, dry} \times \dot{n}_{total, dry} \qquad \text{(Eq. 8)}$$

where $\dot{n}_{total, dry}$ is the total molar flow rate on a dry basis, and $y_{CH_4, dry}$ is the measured dry basis methane mole fraction. The total dry basis molar flow rate, $\dot{n}_{total, dry}$ introduced into the pressure swing adsorption unit 100, may be measured by a flow meter 98 and the molar flow rate of methane, $\dot{n}_{CH_4}$ calculated from the total dry basis molar flow rate and the measure dry basis methane mole fraction. The calculation of the reformate composition may also use a measured flow rate representative of the flow rate of the reformate, e.g. the dry-basis flow rate.

Alternatively, a sample of the reformate may be taken before reacting the reformate in shift reactor 60, the water in the sample condensed and removed, and a dry-basis methane mole fraction, $y_{CH_4, outlet}$, measured, where $$y_{CH_4, outlet} = \frac{\dot{n}_{CH_4}}{\dot{n}_{CO_2} + \dot{n}_{CH_4} + \dot{n}_{CO} + \dot{n}_{H_2} + \dot{n}_{N_2}}. \qquad \text{(Eq. 8 alt)}$$

A constraint based on the water-gas shift equilibrium constant can also be used for determining an effective reformate composition at the outlet of the one or more catalytic reactors:

$$K_{shift}(T_{outlet}) = \frac{\dot{n}_{H_2} \times \dot{n}_{CO_2}}{\dot{n}_{CO} \times \dot{n}_{H_2O}} \qquad \text{(Eq. 9)}$$

where the equilibrium constant is evaluated at the measured outlet temperature, $T_{outlet}$. Any suitable equation for the equilibrium constant for the shift reaction may be used, for example, the equation by Moe "Design of water-gas shift reactors," *Chemical Engineering Progress* 58, pp 33-36, 1962, $K_{shift}(T_{outlet}) = \exp(4577.8/T_{outlet} - 4.33)$.

An algorithm for the solution of a system of nonlinear equations, such as the Levenberg-Marquardt or trust-region-reflective method may be used to calculate the molar flow rates, n, using the equations 4-9. The Levenberg-Marquardt method is described, for example, in Levenberg, "A Method for the Solution of Certain Problems in Least Squares," *Quart. Appl. Math.*, Vol. 2, pp 164-168, 1944, and Marquardt, "An Algorithm for Least-Squares Estimation of Nonlinear Parameters," *SIAM, J. Appl. Math.*, Vol. 11, pp 431-441, 1963.

With the molar flow rates of the reformate species, the equilibrium temperature for the steam-methane reforming reaction can be calculated from equations 1-3 and the reformate pressure, which may be measured or otherwise known. Subsequently the temperature approach to equilibrium may be calculated from the outlet temperature, $T_{outlet}$, and the equilibrium temperature, $T_{equilibrium}$.

The temperature approach to equilibrium calculated using the measured outlet temperature differs from the calculation of the conventional temperature approach to equilibrium since it is recognized that any measured value using a temperature sensor is inaccurate. In the calculation of the conventional temperature approach to equilibrium, the outlet temperature is calculated based on a measured composition of the reformate withdrawn from the catalyst-containing reformer tubes. A sample of the reformate is collected and the concentrations of $H_2$, $CO_2$, $CO$, and $H_2O$ are measured. At temperatures typical for the outlet temperature of the reformer tubes, the water-gas shift reaction is assumed to be at equilibrium. Using the equilibrium constant for the shift reaction, $$K_{shift}(T_{shift, equilibrium}) = \frac{y_{H_2} \times y_{CO_2}}{y_{CO} \times y_{H_2O}},$$

the equilibrium temperature, $T_{shift, equilibrium}$, is calculated from the measured mole fractions, y, of $H_2$, $CO_2$, $CO$, and $H_2O$. Any suitable equation for the equilibrium constant for the shift reaction may be used, for example, the equation by Moe "Design of water-gas shift reactors," *Chemical Engineering Progress* 58, pp 33-36, 1962, $K_{shift}(T_{shift, equilibrium}) = \exp(4577.8/T - 4.33)$. So for example, if the mole fractions of $H_2$, $CO_2$, $CO$, and $H_2O$ are assumed to be 0.6, 0.05, 0.2, and 0.05, respectively, the equilibrium temperature for the shift reaction, $T_{shift, equilibrium}$, is calculated to be 843K.

Likewise, using the measured concentrations of the reformate, the equilibrium temperature for the steam-methane reforming reaction is calculated using equations 1-3 and the outlet pressure. Equation 3 may be used or an alternative expression.

For the conventional temperature approach to equilibrium, the temperature approach to equilibrium is calculated as $\Delta T_{approach, conventional} = T_{shift, equilibrium} - T_{equilibrium}$.

A third of the characterizing steps includes calculating an empirical model-based temperature approach to equilibrium using furnace operating data acquired at each time of the plurality of times in an empirical model based on historical operating data for the reformer or another reformer of the same type for each time of the plurality of times. The empirical model-based temperature approach to equilibrium is a "reference" value taking into account variations in operating conditions for the reformer.

The empirical model for calculating the empirical model-based temperature approach to equilibrium is preferably based on furnace operating data from the reformer being monitored for reduced activity of the reforming catalyst. In the case of a new reformer, historical data is not available and the empirical model may be based on a similar reformer of the same type. A reformer is of the same type as the monitored reformer if the geometry of the catalytic reactors is the same. For example, a reformer having a plurality of catalyst-containing reformer tubes heated by combustion of a fuel and oxidant gas external to the plurality of catalyst-containing reformer tubes is of the same type as another reformer having a plurality of catalyst-containing reformer tubes heated by combustion of a fuel and oxidant gas external to the plurality of catalyst-containing reformer tubes.

The empirical model may be developed from historical data from a reformer. Selected historical data may be used for the development of the empirical model, for example data when the catalyst is known to have high catalytic activity or any and all historical data may be used.

The empirical model relates an empirical temperature approach to equilibrium to several operating parameters for the reformer. Like the temperature approach to equilibrium in the first characterizing step, the empirical temperature approach to equilibrium is based on a measured temperature representative of a temperature at the outlet of the one or more catalytic reactors 20. The measured temperature for developing the empirical model is preferably at the same temperature sensor location as for measuring the outlet temperature in the first characterizing step.

The empirical model may be formulated from historical outlet temperatures, $T_{outlet, historical}$, for the model reformer for a historical plurality of times, and calculated historical equilibrium temperatures, $T_{equilibrium, historical}$, for the model reformer for the historical plurality of times.

The historical equilibrium temperatures, $T_{equilibrium, historical}$, may be calculated in the same manner as described for the equilibrium temperature, $T_{equilibrium}$, using any of equations 1-9.

The historical equilibrium temperatures, $T_{equilibrium, historical}$, may be calculated from the equilibrium constant for the steam-methane reforming reaction at historical reformate compositions representative of reformate withdrawn the one or more catalytic reactors of the model reformer for the historical plurality of times.

The empirical model may be formulated from additional historical operating data including an historical reformate pressure representative of the pressure at the outlet of the one or more catalytic reactors, $P_{outlet, historical}$, an historical flow rate of the steam, $n_{steam, historical}$, and an historical flow rate of the feedstock, $n_{feedstock, historical}$, for the historical plurality of times.

Coefficients for the empirical model may be determined by regressing $\Delta T_{empirical, historical}$ as a function of the historical outlet temperatures, $T_{outlet}$, the historical reformate pressures representative of the pressure at the outlet of the one or more catalytic reactors, $P_{outlet, historical}$, the historical flow rate of the steam, $n_{steam, historical}$, preferably using a steam-to-carbon molar ratio, and the historical flow rate of the feedstock, $n_{feedstock, historical}$.

The function for the empirical model may be a linear or non-linear equation with the coefficients determined by regressing the historical operating data, where $\Delta T_{empirical, historical} = T_{outlet, historical} - T_{equilibrium, historical}$ for the regression.

The empirical model function may include variable derived from additional historical operating data, for example, a steam-to-carbon molar ratio may be used as a variable representative of the steam flow rate. The variable used in the equation for the empirical model may include, for example, hydrocarbon feedstock flow rate, $\dot{n}_{feedstock}$ reformer tube outlet pressure, $P_{outlet}$ steam-to-carbon ratio, S/C, and the temperature representative of a temperature at the outlet of the one or more catalytic reactors, $T_{outlet}$.

The steam-to-carbon molar ratio is a conventional term in the field of hydrogen production and syngas production. The steam-to-carbon ratio may be expressed as a mass ratio or more commonly, a molar ratio.

The steam-to-carbon molar ratio of the feed is the ratio of the molar flow rate of steam in the feed to the molar flow rate of hydrocarbon-based carbon in the feed at the mixing Tee. The molar flow rate of hydrocarbon-based carbon is the molar flow rate of carbon where the carbon is associated with hydrocarbons (i.e. excluding carbon associated with carbon monoxide and carbon dioxide). For example, if the total molar flow rate of the feed is 100 moles/h, and the mole fraction of methane is 0.35, the mole fraction of ethane is 0.1, and the mole fraction of carbon monoxide is 0.05, then the molar flow rate of hydrocarbon-based carbon is 55 moles/h. Methane contributes 35 moles/h of hydrocarbon based carbon. Ethane contributes 20 moles/h of hydrocarbon-based carbon. And carbon monoxide contributes zero moles/h of hydrocarbon based carbon.

An equation or function for the empirical model may be developed by regressing the historical data. In general terms, the empirical temperature approach to equilibrium, $\Delta T_{empirical} = f(T_{outlet}, P_{outlet}, S/C, \dot{n}_{feedstock})$, where $T_{outlet}$ is a measured outlet temperature, $P_{outlet}$ is a measured outlet pressure, S/C is the steam-to-carbon molar ratio, and $\dot{n}_{feedstock}$ is a flow rate of the hydrocarbon feedstock.

The functional form for the empirical model can be linear or nonlinear. A linear example is $$\Delta T_{empirical} = A + B \times \dot{n}_{feedstock} + C \times P_{outlet} + D \times \frac{S}{C} + E \times T_{outlet}.$$

A nonlinear example is $\Delta T_{empirical} = A + B \times (\dot{n}_{feedstock})^b + C \times (P_{outlet})^c + D \times (S/C)^d + E \times (T_{outlet})^e$.

In the development of the empirical model, historical information is used in the functional form and the data regressed to determine the coefficients that best fit the data according to a selected criteria.

For example, for the linear example, $$\Delta T_{empirical, historical} = A + B \times \dot{n}_{feedstock, historical} + C \times P_{outlet, historical} + D \times \frac{S}{C_{historical}} + E \times T_{outlet, historical}.$$

Regression of the historical data to determine the coefficients for the linear and nonlinear equations is routine.

Having the empirical model, for each time, the operating parameters for the reformer are determined through measurements, and the empirical model-based temperature approach to equilibrium is calculated per the third characterizing step.

A fourth of the characterizing steps of the method includes comparing the temperature approach to equilibrium using the measured outlet temperature to the calculated empirical model-based temperature approach to equilibrium for each time of the plurality of times.

The comparison between the temperature approach to equilibrium, $\Delta T_{approach}$ using the measured outlet temperature and the empirical model-based temperature approach to equilibrium, $\Delta T_{empirical}$, may be facilitated using a characteristic operational value $\Delta T_{residual}$ derived from the temperature approach to equilibrium and the calculated empirical model-based temperature approach to equilibrium. The characteristic operational value $\Delta T_{residual}$ may conveniently be a residual temperature approach to equilibrium, $\Delta T_{residual}$, defined as a difference, $\Delta T_{residual} = \Delta T_{approach} - \Delta T_{empirical}$. Other equivalently functioning characteristic operational values may be derived from differences and/or ratios of the temperature approach to equilibrium and the calculated empirical model-based temperature approach to equilibrium to achieve the same result.

The characterizing steps are repeated for the plurality of times in order to monitor the catalytic activity of the reforming catalyst. The characterizing steps may be performed at least once per month, or at least once per week, or at least once per day, or at least once per hour, or at least once per minute during operation of the reformer 10.

The present invention also relates to a method for determining decreased and/or increased catalytic activity of the reforming catalyst. The method for determining decreased and/or increased catalytic activity of reforming catalyst comprises the characterizing steps where the characterizing steps are repeated during a time period where the temperature approach to equilibrium relative to the empirical model-based temperature approach to equilibrium for each time of the plurality of times differs by an amount for a selected period of time, the amount and selected period of time determined to indicate decreased and/or increased activity of the reforming catalyst.

As time progresses from a initial installation of fresh catalyst or a catalyst refurbishment event, the amount by which the temperature approach to equilibrium relative to the empirical model-based temperature approach to equilibrium differs, e.g. $\Delta T_{residual}$, will tend to increase and the increase will be readily apparent. The amount by which the temperature approach to equilibrium relative to the calculated empirical model-based temperature approach to equilibrium for each time differs will, in general, increase as the activity of the catalyst decreases and therefore is an indication of decreased catalytic activity of the reforming catalyst.

Decreased activity of the reforming catalyst can be readily determined by an amount the temperature approach to equilibrium differs from the empirical model-based temperature approach to equilibrium and the period of time the amount exceeds an amount indicating decreased catalytic activity.

A criteria for indicating reduced activity of the reforming catalyst may be established where $\Delta T_{residual}$ increases by more than a selected amount for a selected period of time (i.e. $\Delta T_{residual}$ increases by more than the selected amount from the initial installation of fresh catalyst or catalyst refurbishment event and the increase amount is maintained for a selected period of time).

The amount and selected period of time indicating decreased catalytic activity of the reforming catalyst and whether to act on it, may depend on economic considerations due to decreasing efficiency of the reformer resulting from the decreased catalytic activity. The amount and selected period of time indicating decreased activity of the reforming catalyst may be decided from a predetermined rule for the amount and time period. The selected period of time may be at least one or more days, or at least one or more weeks, or at least one or more months, and may be as long as 6 months or more depending on the severity of the catalyst degradation.

For example, a threshold rule may be applied such that reduced activity is deemed to have occurred the first time that $\Delta T_{residual}$ has increased by a specified amount, such as 3° C. Or, as described in the example, a filtered value of $\Delta T_{residual}$ may be used in judging when reduced activity is deemed to have occurred. Various other rules for detecting a significant degradation in catalyst activity may be developed using the well-known literature on control charts, quickest detection, and linear and nonlinear filtering. These rules include Shewhart control charts, cumulative sum control charts, exponentially weighted moving average control charts, Bayesian quickest detectors, particle filters, and Kalman filters. See, for example: 1) Poor, H. Vincent, and Olympia Hadjiliadis, *Quickest detection*, Cambridge: Cambridge University Press, 2009; 2) Isom, Joshua D. *Exact solution of Bayes and minimax change-detection problems*, Dissertation, University of Illinios at Urbana-Champaign, 2009; 3) Basseville, Michele, and Igor V. Nikiforov, *Detection of abrupt changes: theory and application*, Englewood Cliffs: Prentice Hall, 1993; 4) Arulampalam, M. Sanjeev, et al. "A tutorial on particle filters for online nonlinear/non-Gaussian Bayesian tracking," *IEEE Transactions on signal processing* 50.2 (2002): 174-188; and 5) Harvey, Andrew C. *Forecasting, structural time series models and the Kalman filter*, Cambridge University Press, 1990.

The amount determined to indicate decreased catalytic activity of the reformer catalyst may be an amount corresponding to an increase in a value of a residual temperature approach to equilibrium, $\Delta T_{residual}$, of 3° C. or more during the selected period of time, where $\Delta T_{residual} = \Delta T_{approach} - \Delta T_{empirical}$, where $\Delta T_{approach} = T_{outlet} - T_{equilibrium}$, and corresponds to the temperature approach to equilibrium determined in the second characterizing step, where $T_{outlet}$ is the measured temperature representative of the temperature at the outlet of the one or more catalytic reactors (20), where $T_{equilibrium}$ is a temperature calculated from an equilibrium constant for the steam-methane reforming reaction at a reformate composition representative of the reformate withdrawn from the one or more catalytic reactors (20), and where $\Delta T_{empirical}$ corresponds to the calculated empirical model-based temperature approach to equilibrium.

Increased catalytic activity of the reforming catalyst may also be determined to observe the effect of a catalyst replacement or catalyst refurbishment event. In case of a refurbishment event, additional refurbishment could be applied in case the increase in the catalytic activity is not considered sufficient.

The amount determined to indicate increased catalytic activity of the reformer catalyst may be an amount corresponding to a decrease in a value of a residual temperature approach to equilibrium, $\Delta T_{residual}$, of 3° C. or more during the selected period of time, where $\Delta T_{residual} = \Delta T_{approach} - \Delta T_{empirical}$, where $\Delta T_{approach} = T_{outlet} - T_{equilibrium}$, and corresponds to the temperature approach to equilibrium determined in the second characterizing step, where $T_{outlet}$ is the measured temperature representative of the temperature at the outlet of the one or more catalytic reactors (20), where $T_{equilibrium}$ is a temperature calculated from an equilibrium constant for the steam-methane reforming reaction at a reformate composition representative of the reformate withdrawn from the one or more catalytic reactors (20), and where $\Delta T_{empirical}$ corresponds to the calculated empirical model-based temperature approach to equilibrium.

The present invention also relates to a system for monitoring for changes in the catalytic activity of reforming catalyst in one or more catalytic reactors in a reformer furnace.

With reference to FIG. 1, the system comprises a temperature sensor 26 which is operable to measure an outlet temperature, $T_{outlet}$, where $T_{outlet}$ is representative of a temperature at the outlet of one or more catalytic reactors 20. Temperature sensor 26 is configured to transmit temperature information relating to the measured outlet temperature.

The system also comprises a computing device 200 operable to receive operating information from the reformer furnace 10 including the temperature information from the temperature sensor 26. Computing device 200 is operable to determine a temperature approach to equilibrium for the steam-methane reforming reaction at the outlet of the one or more catalytic reactors 20 over a period of time and for a plurality of times. Computing device 200 is operable to calculate an empirical model-based temperature approach to equilibrium from an empirical model based on historical operating data for the reformer furnace 10 or another reformer furnace for each time of the plurality of times. Computing device 200 is capable of providing an output suitable for comparing the temperature approach to equilibrium to the calculated empirical model-based temperature approach to equilibrium for each time over the period of time in order to monitor for reduced activity of the reforming catalyst.

Computing device 200 may be a programmable logic controller.

Computing device 200 is operable to perform any of the calculations of the present method.

The one or more catalytic reactors 20 may be a plurality of catalyst-containing reformer tubes in a reformer furnace.

The system may further comprise one or more sensors operable to obtain at least a subset of the operating information from the reformer furnace 10 and configured to transmit at least the subset of the operating information to the computing device 200.

The one or more sensors may include a pressure sensor 27 operatively disposed to determine an outlet pressure representative of the pressure at the outlet of the one or more catalytic reactors 20 where the pressure sensor 27 is operatively connected to the computing device 200. The connection between the pressure sensor 27 and the computing device 200 may be hardwired or wireless. The operating information received by the computing device 200 may then include the outlet pressure representative of the pressure at the outlet of the one or more catalytic reactors 20.

The system may further comprise a chemical analyzer 76 operatively disposed to measure a composition of a sample representative of a hydrocarbon feed 75 where the reformer feed gas mixture 15 comprises the hydrocarbon feed 75. If present, the chemical analyzer 76 is operatively connected to the computing device 200. The connection between the chemical analyzer 76 and the computing device may be hardwired or wireless. The operating information received by the computing device 200 may then include the composition of the sample.

The system may further comprise a flow meter 77 operatively disposed to measure a flow rate of the hydrocarbon feed 75 where the flow meter 77 is operatively connected to the computing device 200. The connection between the flow meter 77 and the computing device 200 may be hardwired or wireless. The operating information received by the computing device 200 may then include the flow rate of the hydrocarbon feed 75.

The system may further comprise a flow meter 152 operatively disposed to measure a flow rate of steam 151 where the reformer feed gas mixture 15 comprises the steam 151 where the flow meter 152 is operatively connected to the computing device 200. The connection between the flow meter 152 and the computing device 200 may be hardwired or wireless. The operating information received by the computing device 200 may then include the flow rate of the steam 151.

The system may further comprise a (reformate) chemical analyzer 96 operatively disposed to measure a concentration representative of at least one component in the reformate 25. If present, the chemical analyzer 96 is operatively connected to the computing device 200. The connection between the chemical analyzer 96 and the computing device 200 may be hardwired or wireless. The operating information received by the computing device 200 may then include the concentration representative of the at least one component in the reformate 25. The at least one component may be methane. Chemical analyzer 96 may have a metal oxide semiconductor to determine the concentration of methane. Chemical analyzer 96 may be Model M2A 65-2649RK-CH4 available from RKI Instruments.

The chemical analyzer 96 may be operatively disposed to measure the composition of the reformate 25 prior to the reformate 25 being passed to the shift reactor 60. Alternatively, the chemical analyzer 96 may be operatively disposed to measure a water-depleted reformate 95 withdrawn from separator 90.

The system may further comprise a flow meter 98 operatively disposed to measure a flow rate of the water-depleted reformate 95 where the flow meter 98 is operatively connected to the computing device 200. The connection between the flow meter 98 and the computing device may be hardwired or wireless. The operating information received by the computing device 200 may then include the flow rate of the water-depleted reformate 95.

The system may further comprise a flow meter 108 operatively disposed to measure a flow rate of a hydrogen feed 106 where the reformer feed gas mixture 15 comprises the hydrogen feed 106 where the flow meter 108 is operatively connected to the computing device 200. The connection between the flow meter 108 and the computing device may be hardwired or wireless. The operating information received by the computing device 200 may then include the flow rate of the hydrogen feed 106.

EXAMPLE

The method and system was applied to a steam reformer facility with a catalytic steam-hydrocarbon reformer, like that shown in FIG. 1. The reformer was instrumented with a chemical analyzer 76 for measuring the feedstock composition, a flow meter 77 for measuring the flow rate of the feedstock 75, a flow meter 108 for measuring the flow rate of hydrogen 106 to the hydrodesulphurization unit 155, a flow meter 152 to measure the flow rate of process steam 151, a temperature sensor 26 to measure the collective temperature of the reformate from the plurality of reformer tubes 20, a chemical analyzer 96 for measuring the methane slip on a dry basis, and a pressure sensor 27 for measuring the pressure of the reformate exiting the catalyst-containing reformer tubes 20.

The frequency of obtaining measurements was once per minute during hydrogen production.

Figure 2:
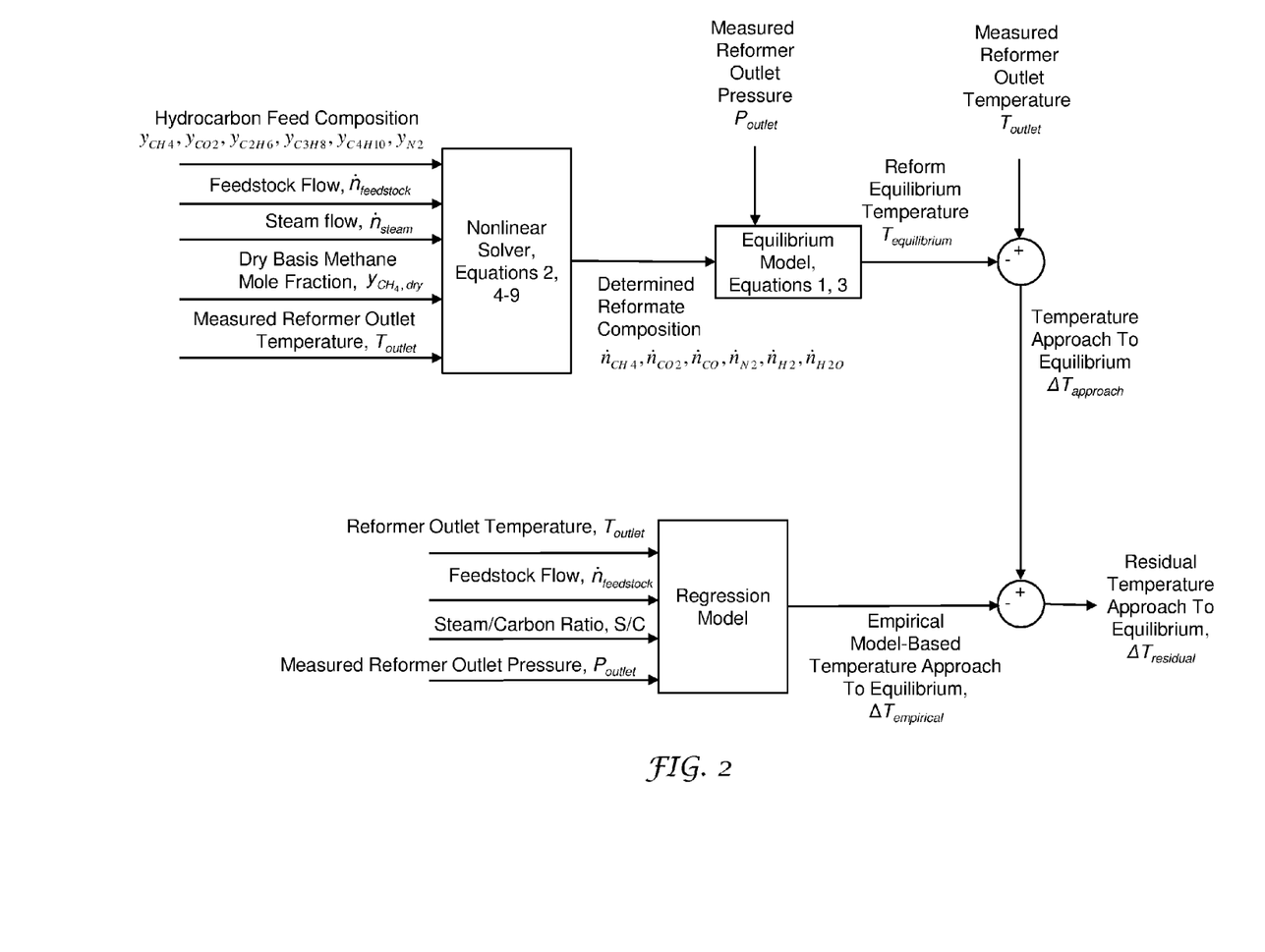
FIG. 2 is a block flow diagram for an example using the method.

A block diagram for the method of the example is shown in FIG. 2. Five sets of inputs were used to determine the reformate composition. The five sets of inputs included 1) a measured composition of the hydrocarbon feed, 2) a measured flow rate of the hydrocarbon feed, 3) a measured steam flow rate, 4) a dry-basis methane concentration at the reformer outlet, and 5) measured reformate outlet temperature. The molar flow rates of $CH_4$, $H_2O$, $CO$, $CO_2$, $H_2$, and $N_2$ at the reformer outlet (a total of six unknowns) was determined by solving a set of six nonlinear equations: 1) hydrogen atom balance (eq. 6), 2) oxygen atom balance (Eq. 5), 3) carbon atom balance (Eq. 4), 4) nitrogen atom balance (Eq. 7), 5) dry basis methane concentration at the reformer exit (Eq. 8 alt.), and 6) water-gas shift equilibrium at the reformer exit (Eq. 9). The set of six nonlinear equations was solved using the MATLAB® function "lsqnonlin". The determined molar flow rates at the reformer outlet, in conjuction with the measured reformer outlet pressure $P_{outlet}$, was used to calculate the reform equilibrium temperature $T_{equilibrium}$ using Equation (1). The temperature approach to equilibrium $\Delta T_{approach}$ was calculated as $\Delta T_{approach} = T_{outlet} - T_{equilibrium}$.

Figure 3:
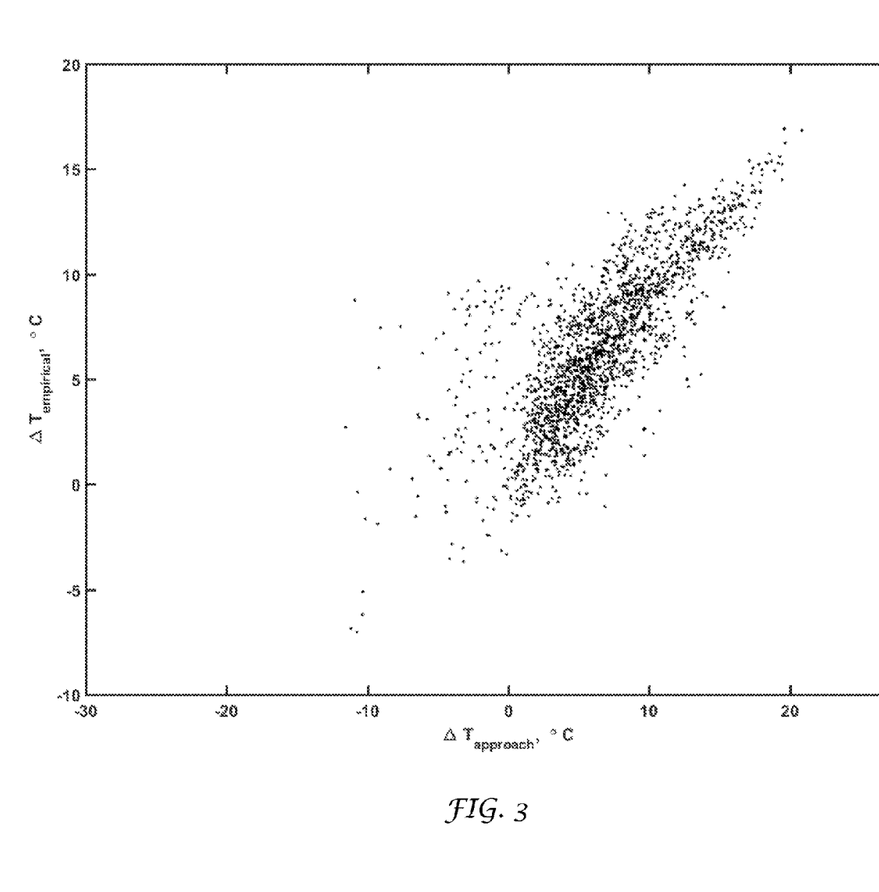
FIG. 3 is a scatter plot of $\Delta T_{empirical}$ versus $\Delta T_{approach}$.

Five years of historical data were used to calculate a linear regression model for $\Delta T_{approach}$ as a function of $T_{outlet}$, $P_{outlet}$, the steam-to-carbon molar ratio (S/C), and the hydrocarbon feedstock flow rate ($\dot{n}_{feedstock}$). The linear regression model is:

$$\Delta T_{emprical} = -689°\text{ C.} - 0.3769 * \dot{n}_{feedstock} - 0.007154 * P_{outlet} + 24.41 * S/C + 0.7540 * T_{outlet}$$

with $P_{outlet}$ measured in units of kPa, $T_{outlet}$ measured in units of ° C., $\dot{n}_{feedstock}$ measured in standard m³/s (standard conditions being 101.325 kPa and 15° C.), and S/C a unitless molar ratio. A statistical test was used to reject, with high confidence, the null hypotheses that each of the regression coefficients is equal to zero. The R-squared statistic associated with the regression model is 0.615, and the root mean squared error of the regression model is 2.94° C. These fit statistics for the regression model are acceptable, because it is known that changes in catalyst activity should affect $\Delta T_{approach}$ but it is not intended that the regression model capture these effects of catalyst activity. As explained above, the purpose of the regression model is to model the normal sensitivity of $\Delta T_{approach}$ to normal changes in process operating conditions. FIG. 3 is a scatter plot of $\Delta T_{emprical}$ versus $\Delta T_{approach}$, which illustrates the normal variability of $\Delta T_{approach}$ and the degree of correlation between $\Delta T_{emprical}$ and $\Delta T_{approach}$.

A residual temperature approach to equilibrium was then calculated as $\Delta T_{residual} = \Delta T_{approach} - \Delta T_{emprical}$.

Figure 4:
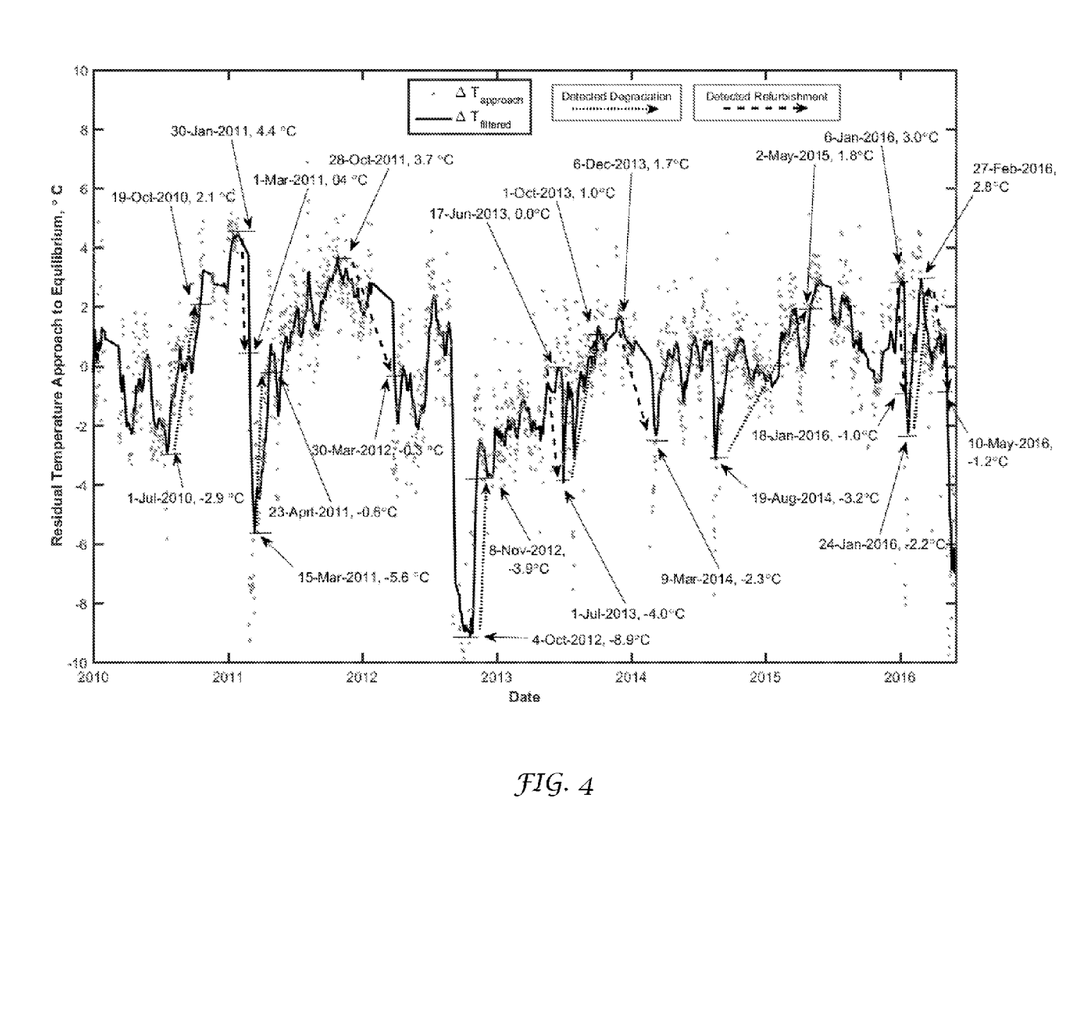
FIG. 4 is a graph of $\Delta T_{approach}$ and of $\Delta T_{filtered}$ versus time, overlaid with indications of detected catalyst degradation or refurbishment events.

Six year's worth of data (from mid-2010 through mid-2016 were used to calculate the residual temperature approach to equilibrium, $\Delta T_{residual}$, on an hourly basis for the facility. FIG. 4 shows a plot of the residual temperature approach to equilibrium, $\Delta T_{residual}$, versus the date for the six year period. A blind test was then used to assess the utility of the method and system for identifying catalyst degradation events and catalyst refurbishment events.

In conducting the validation test, $\Delta T_{residual}$ was used to detect catalyst degradation and refurbishment events using a filtered treand. $\Delta T_{filtered}$, which is defined recursively based on hourly calculated values of $\Delta T_{residual}$. The filtered value at any given hour is equal to 0.90 times the filtered value for the previous hour, plus 0.10 times the current value of $\Delta T_{residual}$:

$$\Delta T_{filtered}(t) = 0.9 * \Delta T_{filtered}(t-1) + 0.1 * \Delta T_{residual}(t).$$

Catalyst degradation was detected when $\Delta T_{filtered}$ increased by 6° C. above the lowest value since the last detected refurbishment. Catalyst refurbishment was detected when $\Delta T_{filtered}$ decreased by 4° C. below the highest value since the last detected catalyst degradation.

The results of the validation test are shown in FIG. 4 along with Table 1. In 10 out of 12 results, the identified catalyst degradation events and catalyst refurbishment events identified using the $\Delta T_{filtered}$ had corresponded to actual catalyst degradation or refurbishment events as determined using plant operating and maintenance logs.

The results of the validation test confirm the utility of the method and system for calculating an effective indicator of catalyst activity.

TABLE 1

| Start Date | End Date | $\Delta T_{filtered}$ (° C.) Start Value | End Value | Change | Detected Catalyst Event | Actual Event/Condition |
|---|---|---|---|---|---|---|
| 1 Jul. 2010 | 19 Oct. 2010 | -2.9 | 2.1 | 5.0 | Degradation | Catalyst skimming was performed in February 2011, hence this would have been preceded by a period of decreasing catalyst activity |
| 30 Jan. 2011 | 1 Mar. 2011 | 4.4 | 0.4 | -4.0 | Refurbishment | Top 40% of the catalyst was replaced in February 2011 |
| 15 Mar. 2011 | 23 Apr. 2011 | -5.6 | -0.6 | 5.0 | Degradation | A period of "break-in" degradation typically follows catalyst replacement |
| 28 Oct. 2011 | 15 Mar. 2012 | 3.7 | -0.3 | -4.0 | Refurbishment | Steaming of the catalyst was performed in February 2012, because hot-band formation was observed in October 2011 |
| 4 Oct. 2012 | 8 Nov. 2012 | -8.9 | -3.9 | 5.0 | Degradation | No significant recorded observation |
| 17 Jun. 2013 | 1 Jul. 2013 | 0 | -4 | -4.0 | Refurbishment | No significant recorded observation |
| 1 Jul. 2013 | 1 Oct. 2013 | -3.97 | 1 | 5.0 | Degradation | Hot band formation observed in October-November 2013 |
| 6 Dec. 2013 | 9 Mar. 2014 | 1.7 | -2.3 | -4.0 | Refurbishment | A complete catalyst change-out was performed in February 2014 |
| 19 Aug. 2014 | 2 May 2015 | -3.2 | 1.8 | 5.0 | Degradation | A complete catalyst change-out was performed in February 2014, this would typically be followed by a period of degradation that one would expect after a new catalyst installation |
| 6 Jan. 2016 | 18 Jan. 2016 | 3 | -1 | -4.0 | Refurbishment | Started operating at higher S/C ratios |
| 24 Jan. 2016 | 27 Feb. 2016 | -2.2 | 2.8 | 5.0 | Degradation | Suspected hot band formation |
| 27 Feb. 2016 | 10 May 2016 | 2.8 | -1.2 | -4.0 | Refurbishment | The plant started operating at reduced rates and higher S/C in May 2016 due to fears of hot band degradation. |

We claim:

1. A method for determining changes in the catalytic activity of reforming catalyst, the method comprising:

(a) introducing a reformer feed gas mixture comprising at least one hydrocarbon and steam into one or more catalytic reactors in a reformer, each of the one or more reactors having an inlet and an outlet, reacting the reformer feed gas mixture in a steam-methane reforming reaction and water-gas shift reaction under reaction conditions effective to form a reformate comprising $H_2$, CO, $CH_4$, and $H_2O$, and withdrawing the reformate from the one or more catalytic reactors;

wherein for a plurality of times, the method comprises
(b) measuring an outlet temperature, $T_{outlet}$, representative of a temperature at the outlet of the one or more catalytic reactors for each time of the plurality of times;
(c) determining a temperature approach to equilibrium for the steam-methane reforming reaction at the outlet of the one or more catalytic reactors for each time of the plurality of times using the measured outlet temperature, $T_{outlet}$;
(d) calculating an empirical model-based temperature approach to equilibrium from reformer operating data and an empirical model based on historical operating data for a model reformer for each time of the plurality of times, wherein the model reformer is the reformer or another reformer; and
(e) comparing the temperature approach to equilibrium to the calculated empirical model-based temperature approach to equilibrium for each time of the plurality of times;
wherein steps (b) through (e) are repeated for the plurality of times.

2. The method according to claim 1 wherein, for each time of the plurality of times, the step of determining the temperature approach to equilibrium for the steam-methane reforming reaction comprises:
determining a reformate composition representative of the reformate withdrawn from the one or more catalytic reactors; and
calculating an equilibrium temperature, $T_{equilibrium}$, from an equilibrium constant for the steam-methane reforming reaction at the reformate composition representative of the reformate withdrawn from the one or more catalytic reactors; and
wherein the temperature approach to equilibrium is calculated from the outlet temperature, $T_{outlet}$, and the equilibrium temperature, $T_{equilibrium}$.

3. The method according to claim 2 wherein the reformer feed gas mixture is formed from a hydrocarbon feed and steam, and wherein the step of determining the reformate composition representative of the reformate withdrawn from the one or more catalytic reactors comprises:
determining a hydrocarbon feed composition representative of a composition of the hydrocarbon feed via composition measurements;
determining a flow rate of the hydrocarbon feed via flow rate measurements of the hydrocarbon feed;
determining a flow rate of the steam via flow rate measurements of the steam; and
calculating the reformate composition using chemical element flow rate balances, the representative hydrocarbon feed composition, the flow rate of the hydrocarbon feed, the flow rate of the steam, and a water-gas shift equilibrium constant evaluated at the measured outlet temperature, $T_{outlet}$.

4. The method according to claim 3 wherein the reformer feed gas mixture is formed from a $H_2$ feed in addition to being formed from the hydrocarbon feed and the steam, and wherein the step of determining the reformate composition representative of the reformate withdrawn from the one or more catalytic reactors comprises:
determining a flow rate of the $H_2$ feed; and
wherein the reformate composition is calculated also using the flow rate of the $H_2$ feed.

5. The method according to claim 3 further comprising:
measuring a methane concentration representative of a concentration of methane in the reformate withdrawn from the one or more catalytic reactors;
wherein the reformate composition is calculated also using the representative methane concentration.

6. The method according to claim 5 further comprising:
measuring a flow rate representative of a flow rate of the reformate;
wherein the reformate composition is calculated also using the representative flow rate of the reformate.

7. The method according to claim 2 further comprising:
measuring a reformate pressure representative of a pressure at the outlet of the one or more catalytic reactors, wherein the equilibrium temperature is calculated using the measured reformate pressure.

8. The method according to claim 1 wherein the empirical model is formulated from historical outlet temperatures, $T_{outlet,\ historical}$, for the model reformer for a historical plurality of times, and calculated historical equilibrium temperatures, $T_{equilibrium,\ historical}$, for the model reformer for the historical plurality of times.

9. The method according to claim 1 wherein step (e) comprises:
calculating a characteristic operational value ($\Delta T_{residual}$) from the temperature approach to equilibrium and the calculated empirical model-based temperature approach to equilibrium, the characteristic operational value including the difference and/or the ratio of the temperature approach to equilibrium and the calculated empirical model-based temperature approach to equilibrium; and
determining whether a change in the characteristic operational value represents an objective increase or decrease in the catalytic activity of the reforming catalyst.

10. A method for determining decreased and/or increased activity of reforming catalyst comprising:
the method of claim 1 wherein steps (b) through (e) are repeated during a time period where the temperature approach to equilibrium relative to the empirical model-based temperature approach to equilibrium for each time of the plurality of times differs by an amount for a selected period of time, the amount and selected period of time determined to indicate decreased and/or increased activity of the reforming catalyst.

11. The method according to claim 10
wherein the amount determined to indicate decreased activity of the reforming catalyst is an amount corresponding to an increase in a value of a residual temperature to equilibrium, $\Delta T_{residual}$, of 3° C. or more during the selected period of time, where $\Delta T_{residual} = \Delta T_{approach} - \Delta T_{empirical}$, where $\Delta T_{approach} = T_{outlet} - T_{equilibrium}$ and corresponds to the temperature approach to equilibrium determined in step (c), where $T_{outlet}$ is the measured temperature representative of the temperature at the outlet of the one or more catalytic reactors (20), where $T_{equilibrium}$ is a temperature calculated from an equilibrium constant for the steam-methane reforming reaction at a reformate composition representative of the reformate withdrawn from the one or more catalytic reactors (20), and where $\Delta T_{empirical}$ corresponds to the calculated empirical model-based temperature approach to equilibrium; and
wherein the amount determined to indicate increased activity of the reforming catalyst is an amount corresponding to a decrease in a value of a residual temperature to equilibrium, $\Delta T_{residual}$, of 3° C. or more during the selected period of time, where $\Delta T_{residual} = \Delta T_{approach} - \Delta T_{empirical}$, where $\Delta T_{approach} = T_{outlet} - T_{equilibrium}$, and corresponds to the temperature approach to equilibrium determined in step (c), where $T_{outlet}$ is the measured temperature representative of the temperature at the outlet of the one or more catalytic reactors (20), where $T_{equilibrium}$ is a temperature calculated from an equilibrium constant for the steam-methane reforming reaction at a reformate composition representative of the reformate withdrawn from the one or more catalytic reactors (20), and where $\Delta T_{empirical}$ corresponds to the calculated empirical model-based temperature approach to equilibrium.

12. A system for determining changes in the catalytic activity of reforming catalyst in one or more catalytic reactors in a reformer, where a reformer feed gas mixture is reacted in a steam-methane reforming reaction and water-gas shift reaction to form a reformate comprising $H_2$, CO, $CH_4$, and $H_2O$, the system comprising:

a temperature sensor operable to measure an outlet temperature, $T_{outlet}$, representative of a temperature at the outlet of the one or more catalytic reactors, the temperature sensor configured to transmit temperature information relating to the measured outlet temperature;

a computing device operable to receive operating information from the reformer including the temperature information from the temperature sensor, the computing device operable to determine a temperature approach to equilibrium for the steam-methane reforming reaction at the outlet of the one or more catalytic reactors over a period of time and for a plurality of times, the computing device operable to calculate an empirical model-based temperature approach to equilibrium from an empirical model based on historical operating data for the reformer or another reformer for each time of the plurality of times, the computing device capable of providing an output suitable for comparing the temperature approach to equilibrium to the calculated empirical model-based temperature approach to equilibrium for each time over the period of time in order to monitor for reduced activity of the reforming catalyst.

13. The system according to claim 12, the system further comprising:

one or more sensors operable to obtain at least a subset of the operating information from the reformer and configured to transmit at least the subset of the operating information to the computing device.

14. The system according to claim 13 wherein the one or more sensors include a pressure sensor operatively disposed to determine an outlet pressure representative of the pressure at the outlet of the one or more catalytic reactors, the pressure sensor operatively connected to the computing device, wherein the operating information received by the computing device includes the outlet pressure representative of the pressure at the outlet of the one or more catalytic reactors.

15. The system according to claim 12, the system further comprising a chemical analyzer operatively disposed to measure a composition of a sample representative of a hydrocarbon feed where the reformer feed gas mixture comprises the hydrocarbon feed, the chemical analyzer operatively connected to the computing device, wherein the operating information received by the computing device includes the composition of the sample.

16. The system according to claim 15, the system further comprising
a flow meter operatively disposed to measure a flow rate of the hydrocarbon feed, the flow meter for measuring the flow rate of the hydrocarbon feed operatively connected to the computing device, wherein the operating information received by the computing device includes the flow rate of the hydrocarbon feed; and/or
a flow meter operatively disposed to measure a flow rate of steam where the reformer feed gas mixture comprises the steam, the flow meter for measuring the flow rate of steam operatively connected to the computing device, wherein the operating information received by the computing device includes the flow rate of the steam.

17. The system according to claim 12, the system further comprising a chemical analyzer operatively disposed to measure a concentration representative of at least one component in the reformate, the chemical analyzer for measuring the concentration representative of the at least one component operatively connected to the computing device, wherein the operating information received by the computing device includes the concentration representative of the at least one component in the reformate.

18. The system according to claim 17 wherein the at least one component includes methane.

19. The system according to claim 12, the system further comprising at least one of
a flow meter operatively disposed to measure a flow rate representative of a flow rate of the reformate, the flow meter for measuring the representative flow rate of the reformate operatively connected to the computing device, wherein the operating information received by the computing device includes the representative flow rate of the reformate; and
a flow meter operatively disposed to measure a flow rate of a hydrogen feed where the reformer feed gas mixture comprises the hydrogen feed, the flow meter for measuring the flow rate of the hydrogen feed operatively connected to the computing device, wherein the operating information received by the computing device includes the flow rate of the hydrogen feed.

* * * * *